US008903041B2

(12) United States Patent
Shimizu

(10) Patent No.: US 8,903,041 B2
(45) Date of Patent: Dec. 2, 2014

(54) X-RAY DIAGNOSTIC APPARATUS

(71) Applicant: Yoshinori Shimizu, Nasushiobara (JP)

(72) Inventor: Yoshinori Shimizu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 149 days.

(21) Appl. No.: 13/710,911

(22) Filed: Dec. 11, 2012

(65) Prior Publication Data

US 2013/0101084 A1    Apr. 25, 2013

Related U.S. Application Data

(63) Continuation of application No. PCT/JP2012/072203, filed on Aug. 31, 2012.

(30) Foreign Application Priority Data

Oct. 7, 2011    (JP) ................................ 2011-223305

(51) Int. Cl.
    *G01N 23/04*    (2006.01)
    *A61B 6/00*    (2006.01)
    *A61B 6/06*    (2006.01)
    *A61B 6/02*    (2006.01)

(52) U.S. Cl.
    CPC ............... *A61B 6/022* (2013.01); *A61B 6/487* (2013.01); *A61B 6/488* (2013.01); *A61B 6/06* (2013.01); *A61B 6/542* (2013.01); *A61B 6/481* (2013.01); *A61B 6/5235* (2013.01); *A61B 6/4417* (2013.01)
    USPC ......................................... 378/62; 378/98.12

(58) Field of Classification Search
    USPC ................... 378/62, 42, 98.11, 98.12
    See application file for complete search history.

(56) References Cited

U.S. PATENT DOCUMENTS

| 8,170,175 | B2 | 5/2012 | Kasuya | |
| 2010/0092062 | A1* | 4/2010 | Gagesch et al. | ............... 382/132 |

FOREIGN PATENT DOCUMENTS

| CN | 1984605 | | 6/2007 |
| JP | 8-164130 A | | 6/1996 |
| JP | 10-234714 A | | 9/1998 |
| JP | 02003265449 A | * | 3/2002 |
| JP | 2003-265449 | | 9/2003 |
| JP | 2010-88803 | | 4/2010 |
| WO | WO 2006/006601 A1 | | 1/2006 |

OTHER PUBLICATIONS

International Search Report issued Dec. 11, 2012, in PCT/JP2012/072203.

(Continued)

*Primary Examiner* — Hoon Song
(74) *Attorney, Agent, or Firm* — Oblon, Spivak, McClelland, Maier & Neustadt, L.L.P.

(57) ABSTRACT

According to one embodiment, an image generation unit generates a first image during a large aperture period and a second image during a small aperture period. An image combining unit generates a composite image based on the latest second image and the specific first image. A display unit displays the composite image in real time. A determination unit determines whether to update the first image based on an index associated with the anatomical positional shift between the first image and the second image. A driving control unit enlarges a aperture to the large aperture, when the determination unit determines to update, and maintains the aperture at the small aperture, when the determination unit determines not to update.

7 Claims, 12 Drawing Sheets

(56) References Cited

OTHER PUBLICATIONS

English translation of International Preliminary Report on Patentability and Written Opinion issued Apr. 17, 2014 in PCT/JP2012/072203.

International Search Report and Written Opinion issued Dec. 11, 2012, in PCT/JP2012/072203 with English Translation of category of cited Documents.

Chinese Office Action issued Sep. 1, 2014, in Patent Application No. 201280002377.X including Search Report with English translation.

* cited by examiner

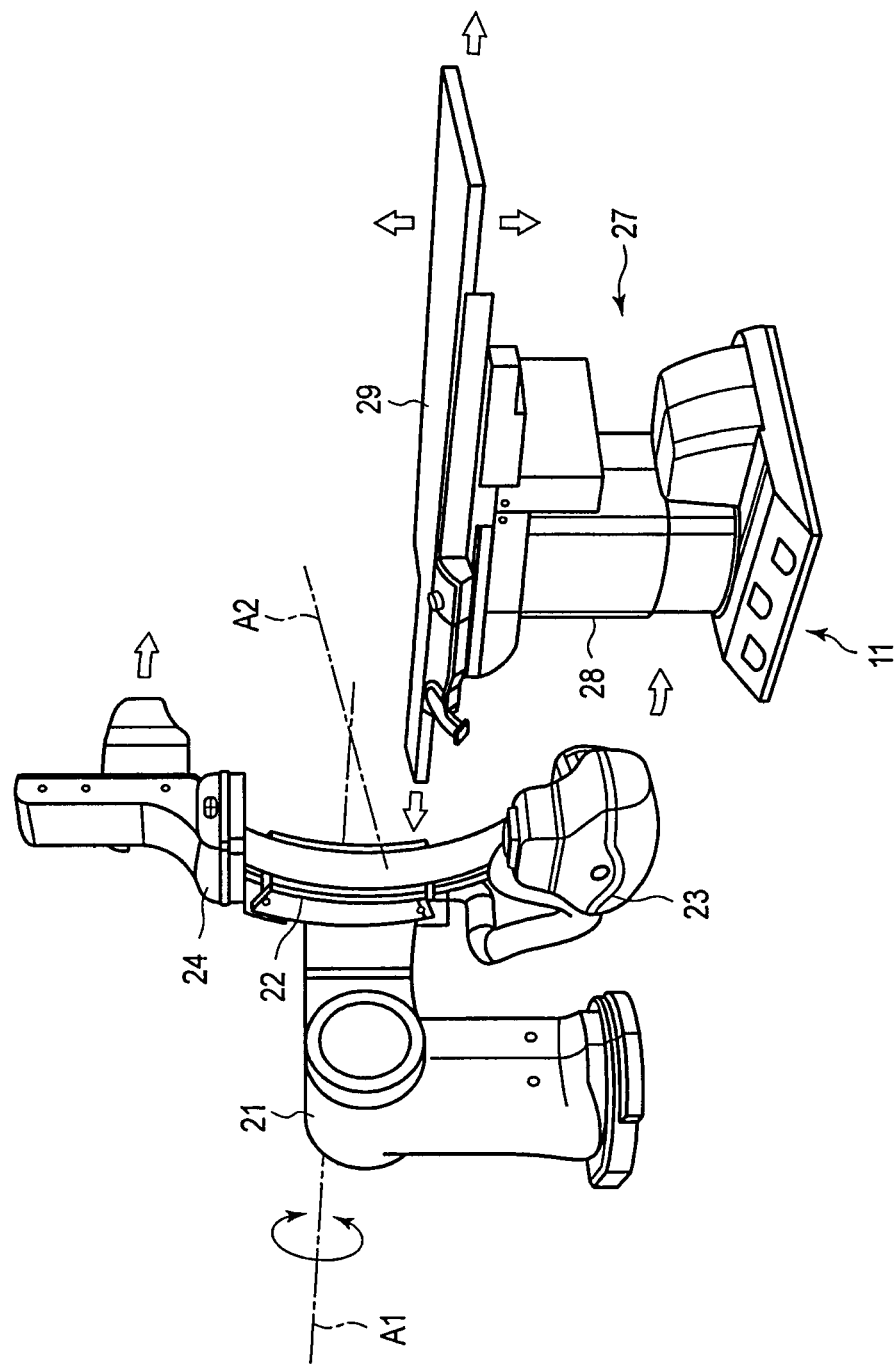
F I G. 2

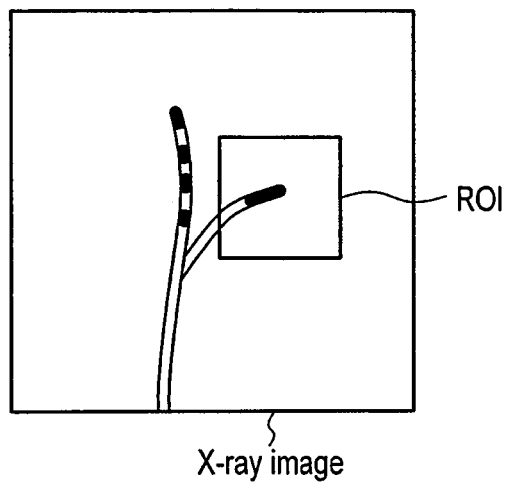
F I G. 3
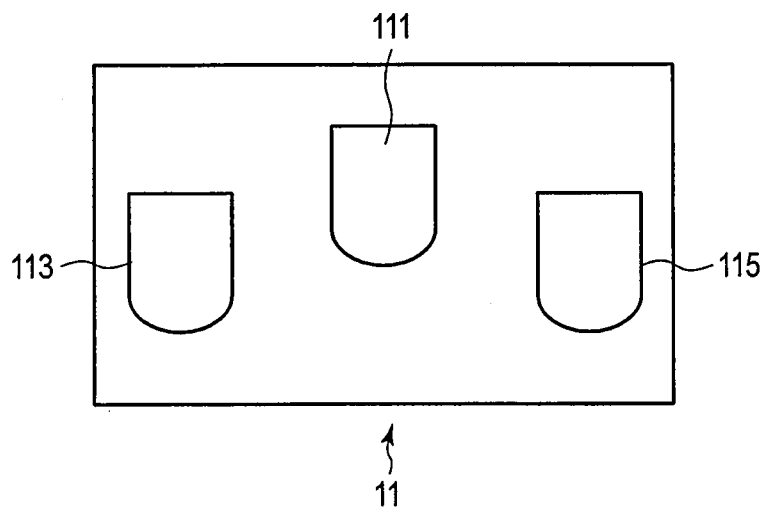
F I G. 4

I2: Composite image

US 8,903,041 B2

X-RAY DIAGNOSTIC APPARATUS

CROSS REFERENCE TO RELATED APPLICATIONS

This application is a Continuation Application of PCT Application No. PCT/JP2012/072203, filed Aug. 31, 2012 and based upon and claiming the benefit of priority from Japanese Patent Application No. 2011-223305, filed Oct. 7, 2011, the entire contents of all of which are incorporated herein by reference.

FIELD

Embodiments described herein relate generally to an X-ray diagnostic apparatus.

BACKGROUND

In an ablation procedure, an X-ray diagnostic apparatus is used to bring a catheter, a guide wire, or the like to a treatment region such as a heart. This ablation procedure often continues for a long period and often takes several hours. Therefore, there have been developed techniques for reducing radiation exposure of a subject and operator at the time of execution of an ablation procedure.

There is available a technique called ROI fluoroscopy which is one of the techniques for exposure reduction. In ROI fluoroscopy, a fluoroscopic image (ROI image) is generated in real time by performing fluoroscopy exclusively for the ROI required for the procedure, and the ROI image is displayed as a dynamic image in real time. There is available a technique as an application of ROI fluoroscopy, which combines an ROI image generated in real time with a wide-range still image generated before ROI fluoroscopy, and displays the composite image as a dynamic image in real time. ROI fluoroscopy can be used for not only an ablation procedure but also for lower extremity and brain operation procedures.

In procedures using ROI fluoroscopy such as ablation procedures, arms and tops are often moved and the visual field sizes are often changed. In addition, since a procedure using ROI fluoroscopy is performed for a long period, the subject often moves. A positional shift therefore often occurs between a still image and an ROI image. In order to eliminate the positional shift between the still image and the ROI image, it is necessary to update the still image. For this reason, the operator re-captures the latest still image upon interrupting ROI fluoroscopy and switching to the general fluoroscopy mode by, for example, changing his/her step from one foot switch to another foot switch. As described above, when updating a still image, the operator operates switches, the operator inevitably interrupts the procedure.

It is an object to provide an X-ray diagnostic apparatus which can improve the procedure efficiency.

BRIEF DESCRIPTION OF THE DRAWINGS

FIG. 2 is a perspective view showing the outer appearance of an imaging mechanism in FIG. 1.

FIG. 3 is a view for explaining ROI setting processing by an operation unit in FIG. 1.

FIG. 4 is a view schematically showing a foot switch unit in FIG. 1.

DETAILED DESCRIPTION

In general, according to one embodiment, an X-ray diagnostic apparatus includes an X-ray tube, an X-ray detector, an aperture-variable collimator mechanism, an image generation unit, a combining unit, a display unit, a determination unit, a control unit. The X-ray tube is configured to generate X-rays. The X-ray detector is configured to detect X-rays generated from the X-ray tube and transmitted through a subject. The aperture-variable collimator mechanism is configured to limit a radiation field of X-rays from the X-ray tube. The image generation unit is configured to repeatedly generate a first X-ray image based on an output from the X-ray detector during a period in which an aperture of the collimator mechanism is a first aperture and to repeatedly generate a second X-ray image based on an output from the X-ray detector during a period in which the aperture is a second aperture smaller than the first aperture. The combining unit is configured to repeatedly generate a composite image based on a latest second X-ray image of the repeatedly generated second X-ray images and a specific first X-ray image of the repeatedly generated first X-ray images for the second X-ray image is generated. The display unit is configured to display the repeatedly generated composite image as a dynamic image in real time. The determination unit is configured to determine whether to update the first X-ray image in the composite image, based on an index associated with an anatomical positional shift between the first X-ray image and the second X-ray image. The control unit is configured to enlarge the aperture of the collimator mechanism from the second aperture to the first aperture by controlling the collimator mechanism when the determination unit determines to update the first X-ray image and to maintain the aperture of the collimator mechanism at the second aperture by controlling the collimator mechanism when the determination unit determines not to update the first X-ray image.

An X-ray diagnostic apparatus according to an embodiment will be described below with reference to the accompanying drawing. Note that this embodiment aims at an X-ray diagnostic apparatus equipped with an ROI fluoroscopy technique.

Figure 1:
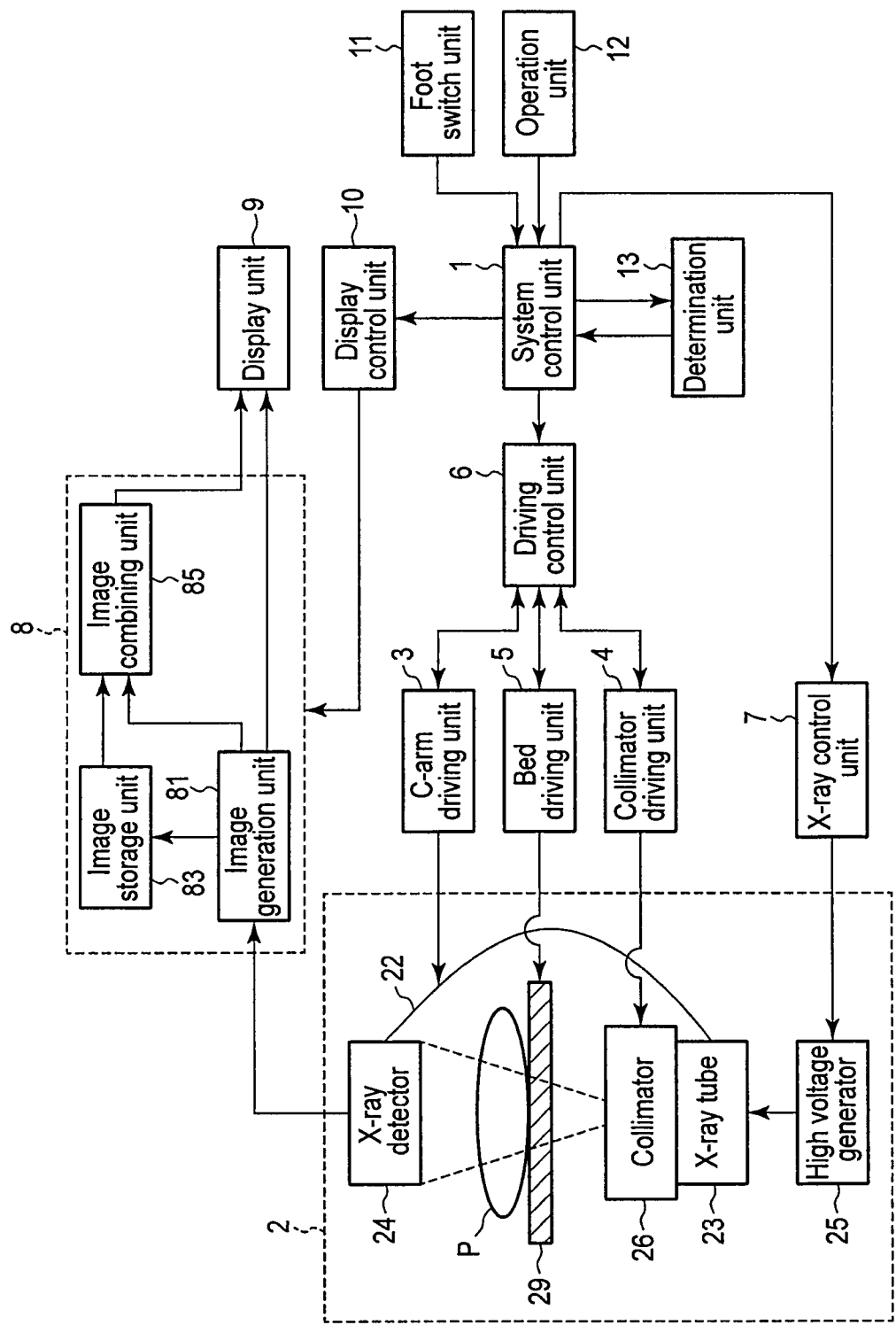
FIG. 1 is a block diagram showing the arrangement of an X-ray diagnostic apparatus according to an embodiment.

The arrangement of an X-ray diagnostic apparatus according to this embodiment will be described first with reference to FIG. 1. FIG. 1 is a block diagram showing the arrangement of the X-ray diagnostic apparatus according to this embodiment. As shown in FIG. 1, the X-ray diagnostic apparatus according to the embodiment includes a system control unit 1 as a main unit, an imaging mechanism 2, a C-arm driving unit 3, a collimator driving unit 4, a bed driving unit 5, a driving control unit 6, an X-ray control unit 7, an image processing unit 8, a display unit 9, a display control unit 10, a foot switch unit 11, an operation unit 12, and a determination unit 13.

FIG. 2 is a view showing the outer appearance of the imaging mechanism 2. As shown in FIGS. 2 and 1, the imaging mechanism 2 includes a C-arm holder 21 rotatably mounted or fixed on a floor. The C-arm holder 21 supports a C-arm 22 so as to allow it to rotate around an axis A1. Upon receiving a driving signal from the C-arm driving unit 3, the C-arm holder 21 rotates the C-arm 22 around the axis A1. The C-arm holder 21 supports the C-arm 22 so as to allow it to slide around an axis A2 perpendicular to the axis A1. Upon receiving a driving signal from the C-arm driving unit 3, the C-arm holder 21 causes the C-arm 22 to slide around the axis A2 along a C shape. The C-arm driving unit 3 supplies a driving signal to the C-arm holder 21 in accordance with a control signal from the driving control unit 6. The intersection between the axis A1 and the axis A2 is called an isocenter. The C-arm 22 rotates around the axis A1 or slides around the axis A2 while the isocenter is always fixed spatially.

The C-arm 22 includes an X-ray tube 23 and an X-ray detector 24 facing each other.

Upon receiving a high voltage and a filament current from a high voltage generator 25, the X-ray detector 24 generates X-rays. The high voltage generator 25 applies a high voltage or supplies a filament current in accordance with a control signal from the X-ray control unit 7. In the fluoroscopy mode, the X-ray tube 23 continuously generates a relatively low dose of X-rays under the control of the X-ray control unit 7. In the radiography mode, the X-ray tube 23 sporadically generates a relatively high dose of X-rays as compared with the fluoroscopy mode under the control of the X-ray control unit 7.

The X-ray detector 24 detects the X-rays generated from the X-ray tube 23. For example, the X-ray detector 24 is implemented by a flat panel display (FPD). The X-ray detector 24 includes a plurality of detection elements arrayed two-dimensionally. Each detection element detects the X-rays generated from the X-ray tube 23, and generates an electrical signal in accordance with the intensity of the detected X-rays. The generated electrical signal is supplied to the image processing unit 8.

A collimator 26 is attached to the X-ray tube 23. The collimator 26 is a movable collimator capable of changing the size and shape of the aperture. More specifically, the collimator 26 movably supports blades made of a material which shields against X-rays. An aperture is defined by the blades. The blades are formed from, for example, lead. The collimator 26 is electrically connected to the collimator driving unit 4. The collimator 26 and the collimator driving unit 4 constitute an aperture-variable collimator mechanism for limiting the radiation field of X-rays from the X-ray tube 23. The collimator 26 moves the blades upon receiving a driving signal from the collimator driving unit 4. The collimator driving unit 4 supplies a driving signal to the collimator 26 in accordance with a control signal from the driving control unit 6. Moving the blades will change the size and shape of the aperture. When the collimator 26 adjusts the size and position of the aperture, the size and position of an X-ray irradiation region onto the detection surface of the X-ray detector 24 are adjusted. For example, the collimator 26 alternately switches the first and second apertures under the control of the driving control unit 6. Assume that the second aperture is smaller in size than the first aperture. In this case, the first and second apertures will be referred to as large and small apertures respectively. As will be described later, the collimator 26 adjusts the sizes and positions of the blades in accordance with when the operator designates or changes the size and position of an ROI with the operation unit 12.

The image processing unit 8 generates an X-ray image associate with a subject P based on an electrical signal from the X-ray detector 24. More specifically, the image processing unit 8 includes an image generation unit 81, an image storage unit 83, and an image combining unit 85. The image generation unit 81 reads out an electrical signal from each detection element of the X-ray detector 24, and generates an X-ray image based on the readout electrical signals. The image generation unit 81 repeatedly generates X-ray images for every predetermined period (e.g., on the order of several ms) while the X-ray tube 23 generates X-rays. The generated X-ray images are supplied to the image storage unit 83, the image combining unit 85, and the display unit 9. In this case, the X-ray image generated by the image generation unit 81 during a period of the large aperture will be referred to as a large-aperture image, and the X-ray image generated by the image generation unit 81 during a period of the small aperture will be referred to as a small-aperture image. The image combining unit 85 generates a composite image by combining a small-aperture image generated in real time with a specific one of repeatedly generated large-aperture images. Typically, a specific large-aperture image is the latest large-aperture image at this time point. That is, a large-aperture image is used for a still image of a composite image. The generated composite image is supplied to the display unit 9. Note that the display control unit 10 switches between supplying an X-ray image (large-aperture image or small-aperture image) to the display unit 9 and supplying a generated composite image to the display unit 9 under the control of the system control unit 1.

The display unit 9 displays an X-ray image from the image generation unit 81 and a composite image from the image combining unit 85. As the display unit 9, it is possible to use a CRT display, liquid crystal display, organic EL display, plasma display, or the like, as needed.

As shown in FIGS. 1 and 2, the imaging mechanism 2 is provided with a bed 27. The bed 27 includes a leg portion 28. The leg portion 28 supports a top 29, on which the subject P is placed, so as to allow it to move in the horizontal and vertical directions. The leg portion 28 is electrically connected to the bed driving unit 5. The bed driving unit 5 supplies a driving signal corresponding to a control signal from the driving control unit 6 to the leg portion 28. The bed driving unit 5 is formed from, for example, a motor such as a stepping motor. Upon receiving a driving signal, the leg portion 28 moves the top 29 in the horizontal or vertical direction in accordance with a driving signal.

The lower portion of the leg portion 28 is provided with the foot switch unit 11. The foot switch unit 11 includes a plurality of switches to be operated by a foot of the operator. For example, the foot switch unit 11 includes a switch for performing X-ray fluoroscopy and a switch for performing ROI fluoroscopy. The details of the foot switch unit 11 will be described later. The operation signal generated by the operation of the foot switch unit 11 is supplied to the foot switch unit 11.

The operation unit 12 accepts various kinds of commands and information inputs from the operator via an input device, and supplies an operation signal corresponding to a received command or information to the system control unit 1. For example, the operation unit 12 sets an ROI in accordance with the instruction input from the operator via the input device. The input device is provided separately from the foot switch unit 11. The input device which can be used include, for example, a keyboard, mouse, buttons, switches, and touch key panel.

The determination unit 13 determines whether to update the large-aperture image in the displayed composite image, based on an index (to be referred as to a positional shift index hereinafter) associated with the anatomical positional shift between the large-aperture image and the small-aperture image. The details of the processing performed by the determination unit 13 will be described later.

The driving control unit 6 controls the C-arm driving unit 3, the collimator driving unit 4, and the bed driving unit 5 under the control of the system control unit 1. For example, the driving control unit 6 supplies a control signal to the C-arm driving unit 3 to move the C-arm 22 to the position designated by the operator. Upon receiving the control signal, the C-arm driving unit 3 supplies a driving signal to the C-arm holder 21 to move the C-arm 22 to the position designated by the operator. The driving control unit 6 supplies a control signal to the bed driving unit 5 to move the top 29 to the position designated by the operator. Upon receiving the control signal, the bed driving unit 5 supplies a driving signal to the leg portion 28 to move the signal line 19 to the position designated by the operator. The driving control unit 6 also supplies a control signal to the collimator driving unit 4 to change the aperture defined by the blades to the size and position designated by the operator. Upon receiving the control signal, the collimator driving unit 4 supplies a driving signal to the collimator 26 to change the aperture to the size and position designated by the operator. If, for example, the determination unit 13 determines to update the large-aperture image, the driving control unit 6 controls the collimator driving unit 4 to enlarge the aperture from the small aperture to the large aperture. If the determination unit 13 determines not to update the large-aperture image, the driving control unit 6 controls the collimator driving unit 4 to maintain the aperture at the small aperture. The driving control unit 6 may control the collimator driving unit 4 to change the aperture in accordance with an instruction from the foot switch unit 11 or the operation unit 12.

The system control unit 1 functions as the main unit of the X-ray diagnostic apparatus according to this embodiment and executes automatic aperture control in ROI fluoroscopy.

Automatic aperture control in ROI fluoroscopy which is performed under the control of the system control unit 1 will be described below. The following description will exemplify an ablation procedure as a concrete example of a clinical application of ROI fluoroscopy. An ablation procedure is one of the cardiac treatment methods. An ablation procedure is a procedure for burning off a small amount of the living tissue of a region as a cause of arrhythmia which is in contact with the distal end of a catheter by supplying a high-frequency current from the distal end of the catheter. An X-ray diagnostic apparatus is used for the navigation of the catheter in an ablation procedure. Ablation procedures tend to continue for long times. In an ablation procedure, therefore, it is possible to effectively reduce the radiation dosage of the operator or subject by using the ROI fluoroscopy mode.

Setting of an ROI by the operation unit 12 will be described first. FIG. 3 is a view for explaining setting of an ROI. As shown in FIG. 3, an ROI is set on the X-ray image displayed on the display unit 9. An X-ray image used for setting an ROI is typically a large-aperture image obtained by X-ray radiography or fluoroscopy. In this case, a large-diameter image is typically an X-ray image generated during a period in which settings are made to irradiate the entire detection surface of the X-ray detector 24 with X-rays.

The operator designates an image region, on the displayed large-aperture image, which is to be observed in real time during a procedure, via an input device such as a mouse. The designated image region is set on the ROI. The positional information of the ROI is supplied to the driving control unit 6 via the system control unit 1.

When an ROI is set, the driving control unit 6 controls the collimator driving unit 4 to change the size and position of the aperture in accordance with the positional information of the ROI. That is, the driving control unit 6 sets an aperture to irradiate only a local region on the X-ray detection surface which corresponds to the ROI with X-rays.

The details of the foot switch unit 11 will be described next. FIG. 4 is a schematic view of the foot switch unit 11. As shown in FIG. 4, the foot switch unit 11 is equipped with, for example, a radiography switch 111, a fluoroscopy switch 113, and an ROI fluoroscopy switch 115.

The radiography switch 111 is a switch for switching the imaging mode to the radiography mode. The system control unit 1 causes the X-ray control unit 7 to execute the radiography mode while the radiography switch 111 is stepped on. In this case, the X-ray control unit 7 controls the high voltage generator 25 to generate a dose of X-rays from the X-ray tube 23 in accordance with the radiography mode. Note that the dose corresponding to the radiography mode is set to be higher than the dose corresponding to the fluoroscopy mode.

The fluoroscopy switch 113 is a switch for switching the image capture mode to the fluoroscopy mode. The system control unit 1 causes the X-ray control unit 7 to execute the fluoroscopy mode while the fluoroscopy switch 113 is stepped on. In this case, the X-ray control unit 7 controls the high voltage generator 25 to generate a dose of X-rays corresponding to the fluoroscopy mode from the X-ray tube 23. In addition, the system control unit 1 controls the collimator driving unit 4 to set the aperture to the large aperture while the fluoroscopy switch 113 is stepped on. That is, a large-diameter image is repeatedly generated while the fluoroscopy switch 113 is stepped on. A large-aperture image is used as the still image of a composite image.

The ROI fluoroscopy switch 115 is a switch for switching the image capture mode to the ROI fluoroscopy mode. The system control unit 1 causes the X-ray control unit 7 to execute the fluoroscopy mode while the ROI fluoroscopy switch 115 is stepped on. In this case, the X-ray control unit 7 controls the high voltage generator 25 to generate a dose of X-rays corresponding to the fluoroscopy mode from the X-ray tube 23. In addition, the system control unit 1 controls the collimator driving unit 4 to set the aperture to an aperture (small aperture) corresponding to an ROI while the ROI fluoroscopy switch 115 is stepped on. That is, a small-aperture image is repeatedly generated while the ROI fluoroscopy switch 115 is stepped on. Each small-aperture image generated while the aperture is set to an aperture corresponding to an ROI will be referred to as an ROI image hereinafter.

Figure 5:
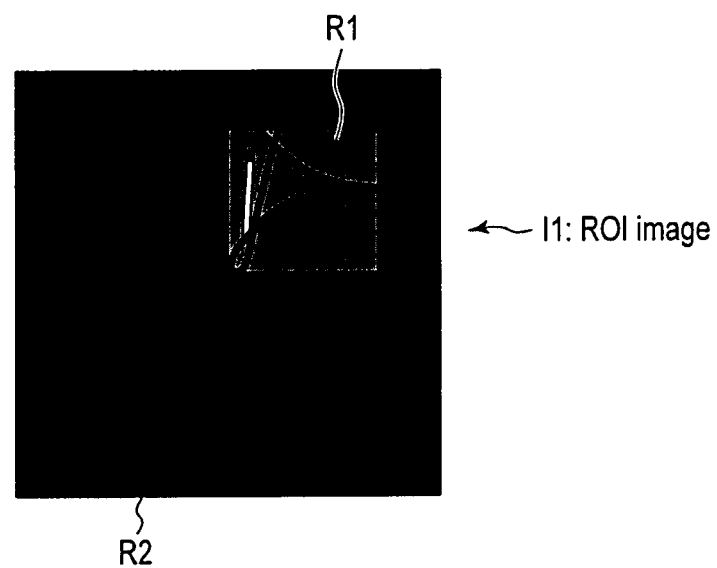
FIG. 5 is a view showing an example of the ROI image generated by an image generation unit in FIG. 1.

FIG. 5 is a view showing an example of an ROI image I1. As shown in FIG. 5, the ROI image I1 includes an ROI region R1 and an empty region R2. The ROI region R1 corresponds to the detection surface region of the X-ray detection surface which is irradiated with X-rays. That is, the ROI region R1 is the image region generated based on an electrical signal from the detection element irradiated with X-rays. The empty region R2 is a portion which is shielded by the blades against X-rays, and corresponds to the detection surface region of the X-ray detection surface which is not irradiated with X-rays. That is, the empty region R2 is the image region generated based on electrical signals from detection elements which are not irradiated with X-rays.

Note that when none of the radiography switch 11, the fluoroscopy switch 113, and the ROI fluoroscopy switch 115 are stepped on, the system control unit 1 instructs the X-ray control unit 7 to stop generating X-rays. Upon receiving the instruction to stop generating X-rays, the X-ray control unit 7 controls the high voltage generator 25 to stop generating X-rays from the X-ray tube 23.

Operation examples of automatic aperture control processing in ROI fluoroscopy according to this embodiment will be described separately next as Example 1, Example 2, and Example 3. Examples 1, 2, and 3 are classified according to the above positional shift index used by the determination unit 13.

Example 1

A positional shift index according to Example 1 is the spatial position of a C-arm 22 or top 29.

Figure 6:
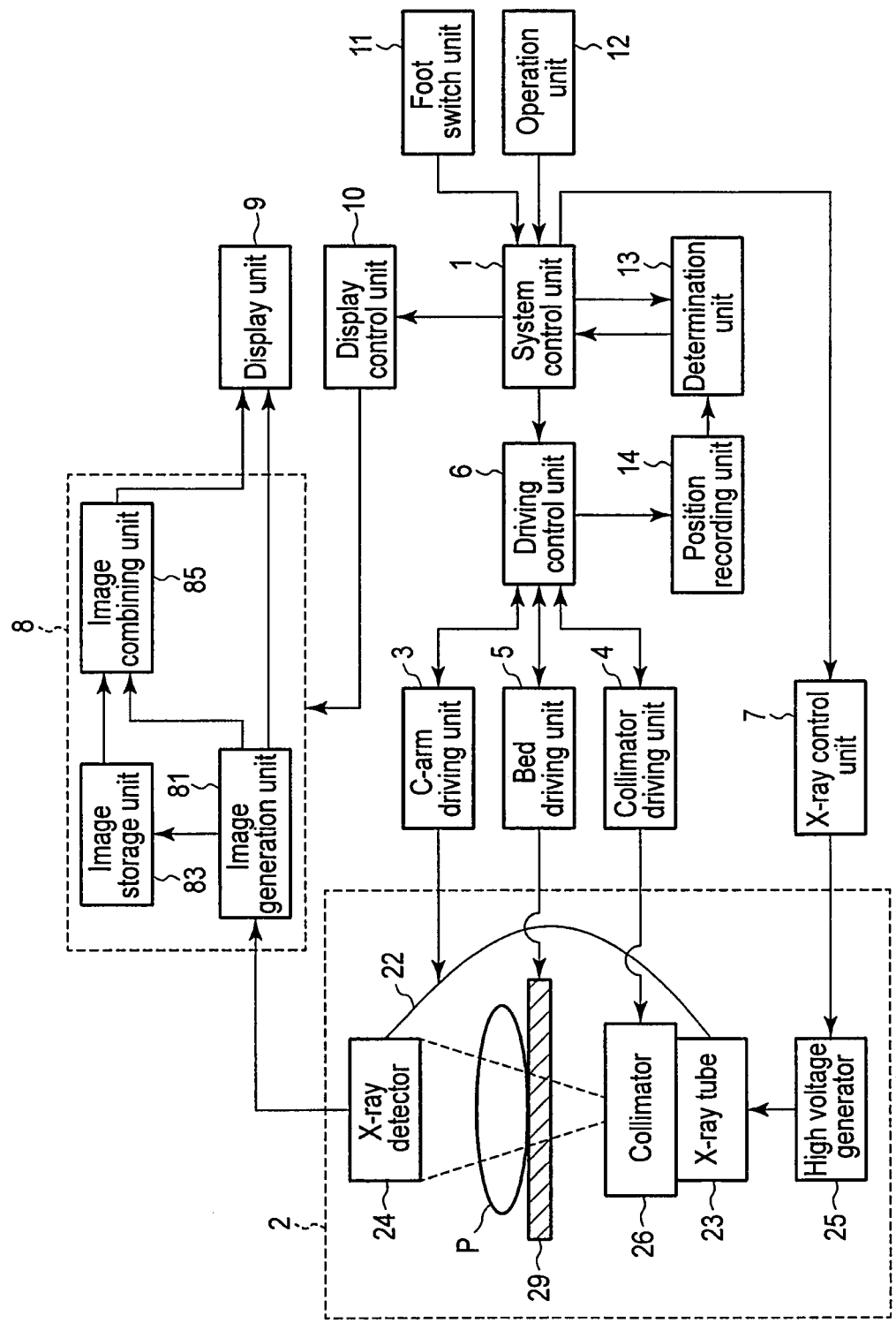
FIG. 6 is a block diagram showing the arrangement of an X-ray diagnostic apparatus according to Example 1 of this embodiment.

FIG. 6 is a block diagram showing the arrangement of an X-ray diagnostic apparatus according to Example 1. As shown in FIG. 6, the X-ray diagnostic apparatus according to Example 1 includes a position recording unit 14 in addition to the units of the X-ray diagnostic apparatus according to this embodiment.

The position recording unit 14 records the positional information of the C-arm 22 and the positional information of the top 29. More specifically, a driving control unit 6 transmits, to the position recording unit 14, the positional information of the C-arm 22 every time the spatial position of the C-arm 22 is changed, and the positional information of the top 29 every time the spatial position of the top 29 is changed. The position recording unit 14 receives the positional information of the C-arm 22 and the positional information of the top 29 from the driving control unit 6, and records the pieces of received positional information on an internal memory or the like. The positional information of the C-arm 22 is information concerning the position (spatial position) of the C-arm 22 in a real space. More specifically, the positional information of the C-arm 22 includes information concerning the rotational angles of the C-arm 22 around an axis A1 and an axis A2. Note that the positional information of the C-arm 22 is not limited to this information. If the C-arm 22 includes a movable axis in addition to the axes A1 and A2, the positional information of the C-arm 22 may include information concerning the spatial position defined by these movable axes. The positional information of the top 29 is information concerning the position (spatial position) of the top 29 in a real space. More specifically, the positional information of the top 29 includes the spatial positions of the top 29 in the vertical and horizontal directions. Assume that the position recording unit 14 associates the time and aperture size (large or small aperture) with each piece of positional information of the C-arm 22 or each piece of positional information of the top 29.

A determination unit 13 determines, every time an ROI image is generated, whether to update a still image, based on a preset threshold and the difference in spatial position between a still image (large-aperture image) when it is generated and an ROI image (small-aperture image) when it is generated. If the determination unit 13 determines to update the still image, the driving control unit 6 enlarges the aperture from the small aperture to the large aperture. If the determination unit 13 determines not to update the still image, the driving control unit 6 maintains the aperture at the small aperture.

Figure 7:
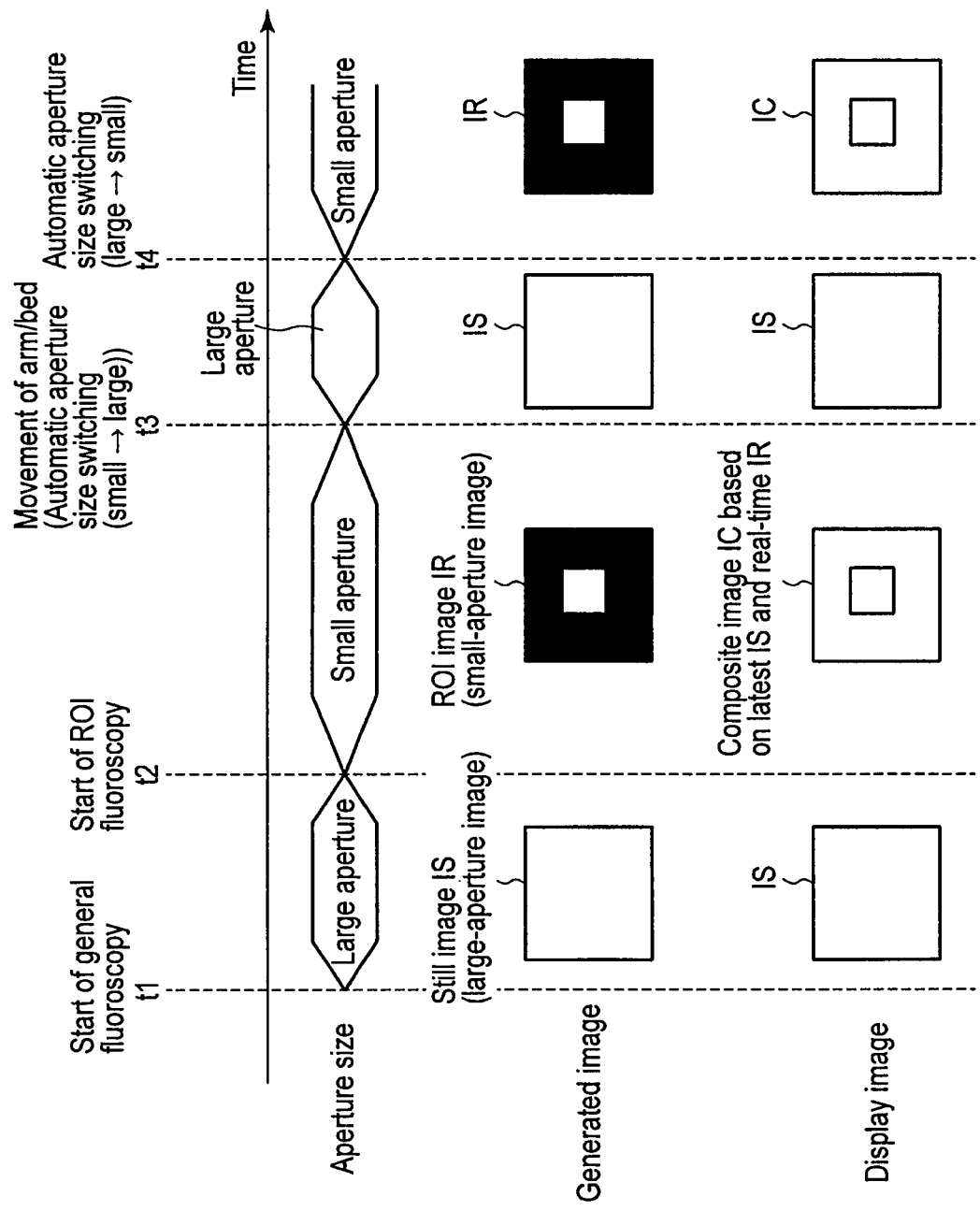
FIG. 7 is a view schematically showing a typical procedure for automatic aperture control processing in ROI fluoroscopy according to Example 1.

An example of automatic aperture control processing in ROI fluoroscopy according to Example 1 will be described below with reference to FIG. 7. FIG. 7 is a view schematically showing a typical procedure for automatic aperture control processing in ROI fluoroscopy according to Example 1.

First of all, the operator steps on the fluoroscopy switch at time t1 to perform X-ray fluoroscopy under the control of the driving control unit 6. As described above, in the fluoroscopy mode, the aperture is set to the large aperture, an image generation unit 81 repeatedly generates a large-aperture image in real time, and a display unit 9 displays a large-aperture image IS as a dynamic image in real time. This large-aperture image is typically generated to be used for the still image of a composite image to be generated afterward. The operator observes the large-aperture image displayed on the display unit 9 and determines whether a large-aperture image suitable for a still image has been generated. In addition, the operator may set an ROI on a large-aperture image via an operation unit 12. Note that the operator may set an ROI before time t1.

Upon determining that a large-aperture image suitable for a still image has been generated, the operator steps off the fluoroscopy switch and steps on the ROI fluoroscopy switch (time t2). The large-aperture image (LHI: last holding image) displayed on the display unit 9 at the time when the operator steps on the ROI fluoroscopy switch is displayed as a still image on the display unit 9. An image storage unit 83 stores this still image. When the operator steps on the ROI fluoroscopy switch, the driving control unit 6 starts ROI fluoroscopy. More specifically, the driving control unit 6 controls a collimator driving unit 4 to reduce the aperture of a collimator 26 from the large aperture to the small aperture. An X-ray control unit 7 also controls a high voltage generator 25 to continuously generate X-rays having a dose for fluoroscopy from an X-ray tube 23. Irradiating a subject P with X-rays upon limiting the irradiation to the small aperture corresponding to the ROI can reduce the radiation dosage of the subject P or the like. During the ROI fluoroscopy mode, the image generation unit 81 repeatedly generates an ROI image IR in real time. Every time the ROI image IR is generated, an image combining unit 85 repeatedly generates a composite image IC based on the ROI image IR and the large-aperture image IS stored as a still image in the image storage unit 83. The display unit 9 displays the generated composite image IC as a dynamic image in real time.

Figure 8:
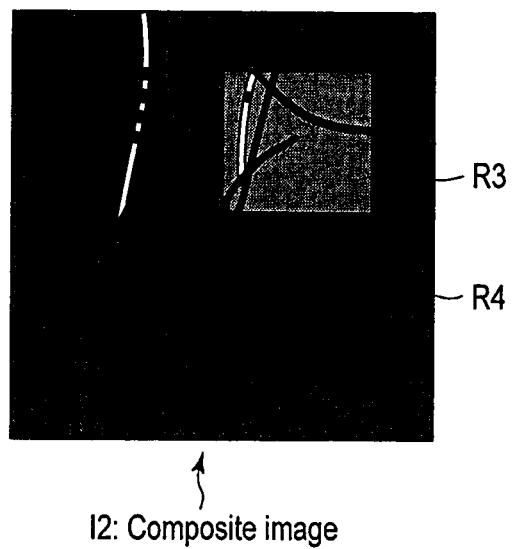
FIG. 8 is a view showing an example of the composite image generated by an image combining unit in FIG. 7.

FIG. 8 is a view showing an example of a composite image I2. As shown in FIG. 8, the composite image I2 includes an ROI image region R3 and a still image region R4. The ROI image region R3 corresponds to the ROI region in the ROI image generated in real time. The still image region R4 corresponds to an image region other than the ROI region of the still image. That is, the ROI image region R3 in the composite image I2 is displayed as a dynamic image, and the still image region R4 is displayed as a still image. Combining and displaying an ROI image and a still image in this manner can display only a target ROI as a dynamic image in real time while allowing the operator to easily comprehend the position of the ROI in a still image. It is therefore possible to reduce the radiation dosage more than in the fluoroscopy mode while maintaining the operability in the fluoroscopy mode.

For example, the image combining unit 85 combines an ROI region in an ROI image and an image region other than an ROI region in a still image by using a superimposing technique. This generates a composite image like that obtained by pasting an ROI region cut from an ROI image to a still image.

According to the above description, the apparatus performs fluoroscopy only with the small aperture at the time of ROI fluoroscopy. However, this embodiment is not limited to this. For example, the apparatus may perform fluoroscopy with the large aperture for only a preset time at the start of ROI fluoroscopy. The preset time is preferably set to a relatively short period, e.g., 1 sec. The display unit 9 displays the large-aperture image generated at the start of ROI fluoroscopy. When the preset time has elapsed, the driving control unit 6 switches the large aperture to the small aperture, and the X-ray control unit 7 performs fluoroscopy with the small aperture, as described above.

In some case, the apparatus moves the C-arm 22 or the top 29 in accordance with an instruction issued by the operator via the operation unit 12 during the execution of the ROI fluoroscopy mode. Since a still image is an image generated in the past, when the C-arm 22 or top 29 moves, an anatomical positional shift occurs between an ROI image and a still image. Even if the operator observes the composite image based on the ROI image and the still image between which the positional shift has occurred, the operator cannot properly determine the position of a catheter or the like. Displaying the composite image based on the ROI image and the still image between which the positional shift has occurred will degrade operability.

The X-ray diagnostic apparatus according to this embodiment eliminates the above problem accompanying the movement of the C-arm 22 or top 29 by using positional information concerning the spatial position of the C-arm 22 or top 29. For this purpose, the position recording unit 14 records the spatial position of the C-arm 22 and the spatial position of the top 29 during an ablation procedure. Recording timings may be set as follows. The position recording unit 14 may record the spatial position of the C-arm 22 and the spatial position of the top 29 at predetermined time intervals or every time the C-arm 22 or the top 29 is moved. The position recording unit 14 records each spatial position in association with the time and the identifier of an aperture size (large or small aperture).

The determination unit 13 determines whether to update the still image, by using positional information concerning the spatial position recorded on the position recording unit 14. The determination unit 13 individually determines a change in the spatial position of the C-arm 22 and a change in the spatial position of the top 29. Note that the determination unit 13 may perform the determination processing at predetermined time intervals or every time the C-arm 22 or the top 29 is moved.

In the case of the C-arm 22, the determination unit 13 performs the determination in the following manner. In the determination processing associated with the C-arm 22, the determination unit 13 reads out the real-time spatial position of the C-arm 22 and the spatial position of the C-arm 22 at a reference time from the position recording unit 14. The spatial position at the reference time is set to the spatial position of the C-arm 22 at the time of generation of a large-aperture image. For example, the spatial position at the reference time is set to the spatial position of the C-arm 22 at the time point when the ROI fluoroscopy switch is stepped on. If the ROI fluoroscopy switch has been stepped on a plurality of number of times, the spatial position of the C-arm 22 at the latest time when the switch was stepped on is set to the spatial position at the reference time. Upon reading out the spatial positions, the determination unit 13 calculates the difference between the real-time spatial position of the C-arm 22 and the spatial position of the C-arm 22 at the reference time. The determination unit 13 then determines whether the calculated difference exceeds a threshold for the C-arm 22. The operator can arbitrarily set a threshold via the operation unit 12. For example, it is preferable to set a threshold to the maximum value or the like of the allowable range of positional shifts for the operator. If no positional shift is allowed between an ROI image and a still image, the threshold is preferably set to 0.

In the case of the top 29, the determination unit 13 performs the determination in the same manner as in the case of the C-arm 22. In the determination processing associated with the top 29, the determination unit 13 reads out the real-time spatial position of the top 29 and the spatial position of the top 29 at a reference time from the position recording unit 14. The spatial position at the reference time is set to the spatial position of the top 29 at the time of generation of a large-aperture image. For example, the spatial position at the reference time is set to the spatial position of the top 29 at the time point when the ROI fluoroscopy switch is stepped on. If the ROI fluoroscopy switch was stepped on a plurality of number of times, the spatial position of the top 29 at the latest time when the switch was stepped on is set to the spatial position at the reference time. Upon reading out the spatial positions, the determination unit 13 calculates the difference between the real-time spatial position of the top 29 and the spatial position of the top 29 at the reference time. The determination unit 13 then determines whether the calculated difference exceeds a threshold for the top 29. The operator can arbitrarily set a threshold via the operation unit 12. Note that thresholds are individually set for the C-arm 22 and the top 29.

Upon determining that the difference does not exceed the threshold, the determination unit 13 determines that there is no need to update the still image. More specifically, upon determining that both the differences associated with the C-arm 22 and the top 29 do not exceed the thresholds, the determination unit 13 determines that there is no need to update the still image. In this case, the driving control unit 6 controls the collimator driving unit 4 to maintain the aperture at the small aperture. The X-ray control unit 7 controls the high voltage generator 25 to continuously generate X-rays for fluoroscopy.

Upon determining that the differences exceed the thresholds (time t3), the determination unit 13 determines to update the still image. More specifically, upon determining that at least one of the differences associated with the C-arm 22 and the top 29 does not exceed the corresponding threshold, the determination unit 13 determines that there is no need to update the still image. In this case, the driving control unit 6 controls the collimator driving unit 4 to automatically enlarge the aperture from the small aperture to the large aperture. The X-ray control unit 7 controls the high voltage generator 25 to repeatedly generate X-rays for fluoroscopy from the X-ray tube 23. With this operation, the image generation unit 81 generates the large-aperture image IS. Since the new large-aperture image IS used to update the still image, at least one large-aperture image may be generated. Note that switching from the large aperture to the small aperture in accordance with the determination result obtained by the determination unit 13 is performed without making the operator change his/her step from the ROI fluoroscopy switch to the fluoroscopy switch. That is, the apparatus switches from the small aperture to the large aperture, while the ROI fluoroscopy switch is kept stepped on, to generate the new large-aperture image IS. The image storage unit 83 stores the generated new large-aperture image IS as a new still image.

After the lapse of a predetermined period since the aperture was enlarged to the large aperture (time t4), the driving control unit 6 automatically switches to the ROI fluoroscopy mode. That is, the driving control unit 6 controls the collimator driving unit 4 to automatically reduce the aperture from the large aperture to the small aperture. The X-ray control unit 7 controls the high voltage generator 25 to repeatedly generate X-rays for fluoroscopy. Note that it is preferable to set this predetermined period to a period during which at least one large-aperture image can be generated. During the ROI fluoroscopy mode, the image generation unit 81 repeatedly generates an ROI image IR in real time. Every time the ROI image IR is generated, the image combining unit 85 repeatedly generates the composite image IC based on the ROI image IR and the large-aperture image IS stored as a new still image in the image storage unit 83 in real time. The display unit 9 displays the generated composite image IC as a dynamic image in real time.

According to the above description, the aperture is automatically switched from the large aperture to the small aperture after the lapse of the predetermined period. However, Example 1 is not limited to this. For example, the aperture may be switched from the large aperture to the small aperture when the operator re-steps on the ROI fluoroscopy switch. This makes it possible to set, as a still image on a composite image, the large-aperture image determined as an image suitable for a still image by the operator.

This is the end of the description of an operation example according to Example 1.

As described above, the X-ray diagnostic apparatus according to Example 1 automatically switches the aperture from the small aperture to the large aperture when the positional shift amount between the spatial position of the C-arm 22 or top 29 at the time of generation of a still image and the real-time spatial position of the C-arm 22 or top 29 exceeds a threshold. In the X-ray diagnostic apparatus according to Example 1, this can automatically update a still image when an anatomical positional shift occurs between the still image and an ROI image, thereby providing a composite image with a small anatomical positional shift amount. It is therefore not necessary for the operator to change his/her step from one switch to another switch at this time. The operator can therefore update a still image without giving any thought to changing his/her step from one switch to another switch and concentrate on the ablation procedure.

Example 2

A positional shift index according to Example 2 is a real-time X-ray generation duration time in the ROI fluoroscopy mode.

Figure 9:
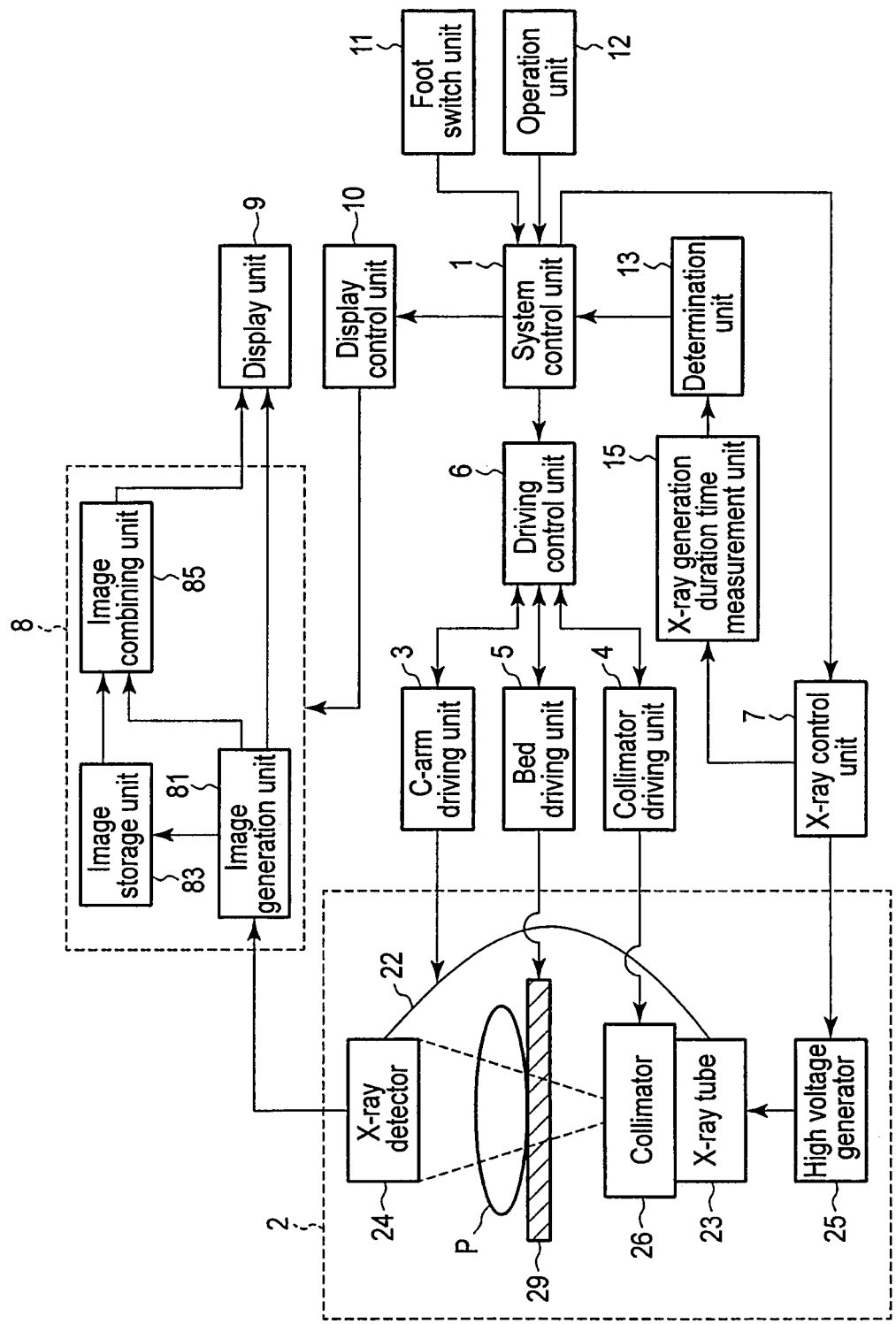
FIG. 9 is a block diagram showing the arrangement of an X-ray diagnostic apparatus according to Example 2 of this embodiment.

FIG. 9 is a block diagram showing the arrangement of an X-ray diagnostic apparatus according to Example 2. As shown in FIG. 9, the X-ray diagnostic apparatus according to Example 2 includes an X-ray generation duration time measurement unit 15 in addition to the units of the X-ray diagnostic apparatus according to this embodiment.

The X-ray generation duration time measurement unit 15 repeatedly measures the time (to be referred to as an X-ray generation duration time hereinafter) during which X-rays are continuously generated from the start time of the ROI fluoroscopy mode. If the X-ray generation duration time is relatively long, it is expected that a subject P will move. In other words, if the X-ray generation duration time is relatively long, it can be estimated that an anatomical positional shift has occurred between an ROI image and a still image. The measured X-ray generation duration time is supplied to a determination unit 13.

The determination unit 13 determines whether to update a still image, based on the X-ray generation duration time, every time an ROI image is generated. If the determination unit 13 determines to update the still image, a driving control unit 6 enlarges the aperture from the small aperture to the large aperture. If the determination unit 13 determines not to update the still image, the driving control unit 6 maintains the aperture at the small aperture.

Figure 10:
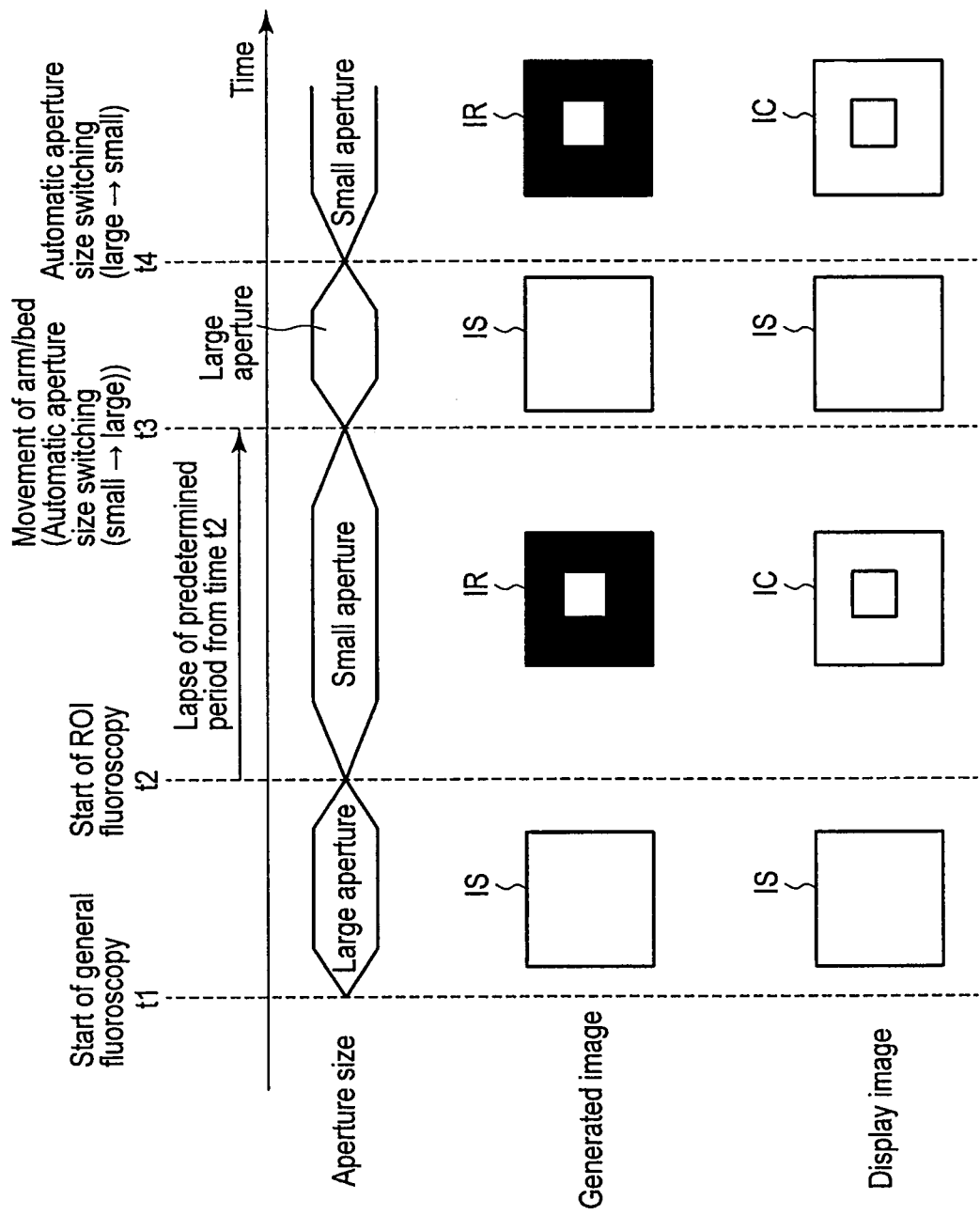
FIG. 10 is a view schematically showing a typical procedure for automatic aperture control processing in ROI fluoroscopy according to Example 2.

An example of automatic aperture control processing in ROI fluoroscopy according to Example 2 will be described below with reference to FIG. 10. FIG. 10 is a view schematically showing a typical procedure for automatic aperture processing in ROI fluoroscopy according to Example 2. The same processing contents as automatic aperture control processing in ROI fluoroscopy according to Example 1 will be briefly described.

First of all, at time t1, the operator steps on the fluoroscopy switch, and the apparatus performs X-ray fluoroscopy under the control of the driving control unit 6. As described above, in the fluoroscopy mode, the aperture is set to the large aperture, and an image generation unit 81 repeatedly generates a large-aperture image in real time. A display unit 9 displays a large-aperture image IS as a dynamic image in real time.

Upon determining that a large-aperture image suitable for a still image is generated, the operator steps off the fluoroscopy switch and steps on the ROI fluoroscopy switch (time t2). The large-aperture image displayed on the display unit 9 when the operator steps on the ROI fluoroscopy switch is displayed as a still image on the display unit 9. When the operator steps on the ROI fluoroscopy switch, the driving control unit 6 starts ROI fluoroscopy. During the ROI fluoroscopy mode, the image generation unit 81 repeatedly generates an ROI image IR in real time. Every time the ROI image IR is generated, an image combining unit 85 repeatedly generates a composite image IC based on the ROI image IR and the large-aperture image IS stored as a still image in an image storage unit 83 in real time. The display unit 9 displays the generated composite image IC as a dynamic image in real time.

When the operator steps on the ROI fluoroscopy switch (time t2), the X-ray generation duration time measurement unit 15 repeatedly measures an X-ray generation duration time. The determination unit 13 determines, in the ROI fluoroscopy mode, whether the measured X-ray generation duration time exceeds a predetermined time set in advance. The operator can arbitrarily set the predetermined time town arbitrary value via the operation unit 12.

Upon determining that the X-ray generation duration time does not exceed the predetermined time, the determination unit 13 determines that there is no need to update the still image. In this case, the driving control unit 6 controls the collimator driving unit 4 to maintain the aperture at the small aperture. An X-ray control unit 7 controls a high voltage generator 25 to make it continuously generate X-rays for fluoroscopy.

Upon determining that the X-ray generation duration time has exceeded the predetermined time (time t3), the determination unit 13 determines to update the still image. In this case, the driving control unit 6 controls the collimator driving unit 4 to automatically enlarge the aperture from the small aperture to the large aperture. The X-ray control unit 7 controls the high voltage generator 25 to make an X-ray tube 23 repeatedly generate X-rays for fluoroscopy. With this operation, the image generation unit 81 generates the large-aperture image IS.

After the lapse of a predetermined period since the aperture was enlarged to the large aperture (time t4), the driving control unit 6 automatically switches to the ROI fluoroscopy mode. That is, the driving control unit 6 controls the collimator driving unit 4 to automatically reduce the aperture from the large aperture to the small aperture. The X-ray control unit 7 controls the high voltage generator 25 to repeatedly generate X-rays for fluoroscopy. During the ROI fluoroscopy mode, the image generation unit 81 repeatedly generates the ROI image IR in real time. Every time the ROI image IR is generated, the image combining unit 85 repeatedly generates the composite image IC based on the ROI image IR and the large-aperture image IS stored as a new still image in the image storage unit 83 in real time. The display unit 9 displays the generated composite image IC as a dynamic image in real time.

This is the end of the description of an operation example according to Example 2.

As described above, the X-ray diagnostic apparatus according to Example 2 automatically switches the aperture from the small aperture to the large aperture when the X-ray generation duration time from the start of ROI fluoroscopy mode exceeds a predetermined period. This allows the X-ray diagnostic apparatus according to Example 2 to automatically update a still image when it is estimated that an anatomical positional shift will occur between the still image and an ROI image, thereby providing a composite image with a small anatomical positional shift amount. It is therefore not necessary for the operator to change his/her step from one switch to another switch at this time. The operator can therefore update a still image without giving any thought to changing his/her step from one switch to another switch and concentrate on the ablation procedure.

Example 3

A positional shift index according to Example 3 is a real-time X-ray non-generation duration time in the ROI fluoroscopy mode.

Figure 11:
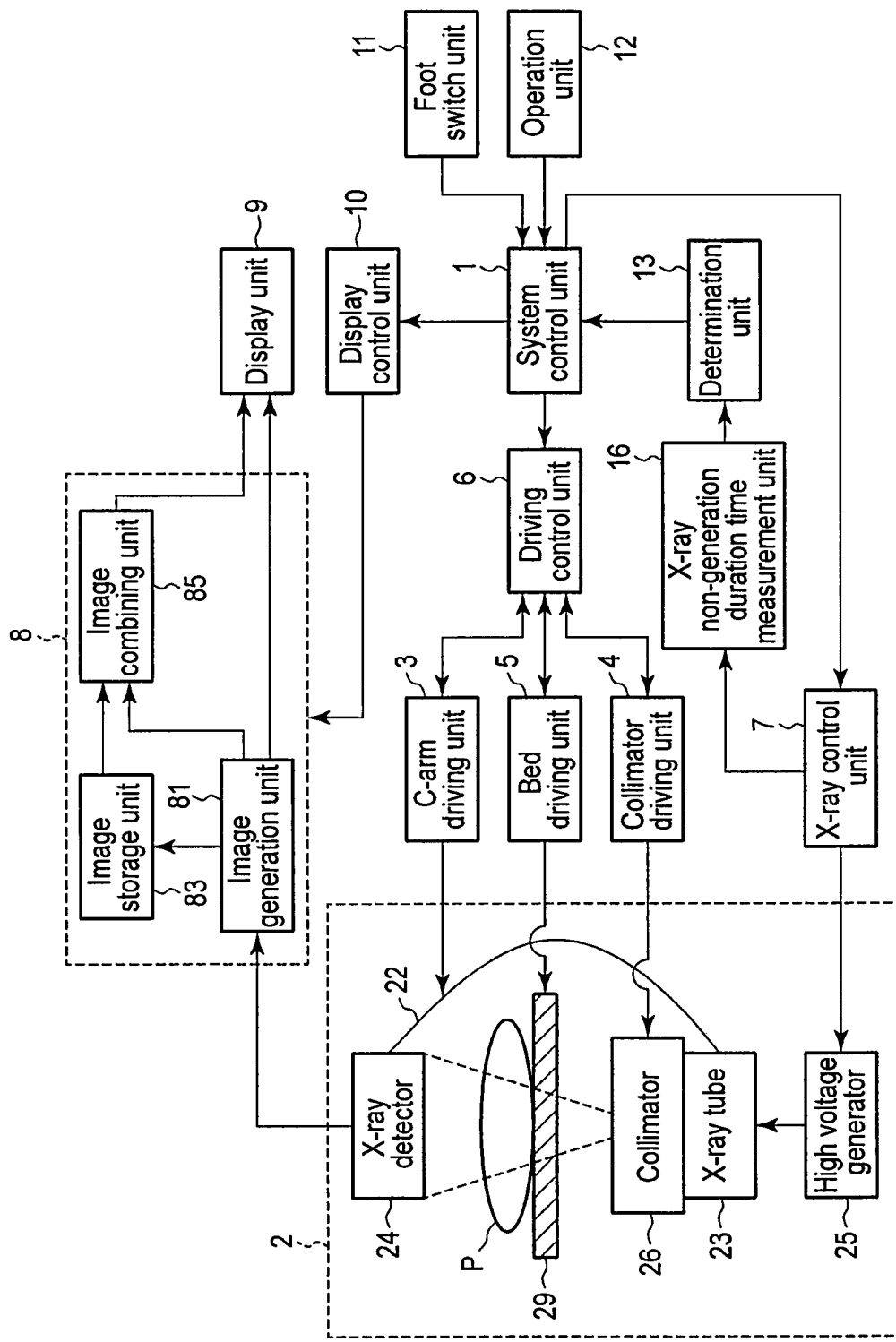
FIG. 11 is a block diagram showing the arrangement of an X-ray diagnostic apparatus according to Example 3 of this embodiment.

FIG. 11 is a block diagram showing the arrangement of an X-ray diagnostic apparatus according to Example 3. As shown in FIG. 11, the X-ray diagnostic apparatus according to Example 3 includes an X-ray non-generation duration time measurement unit 16 in addition to the units of the X-ray diagnostic apparatus according to this embodiment.

The X-ray non-generation duration time measurement unit 16 repeatedly measures the time (to be referred to as the X-ray non-generation duration time hereinafter) during which no X-rays are continuously generated from the point of time when the generation of X-rays in the ROI fluoroscopy mode is stopped. If the X-ray non-generation duration time is relatively long, it is expected that a subject P has moved or a C-arm 22 or top 29 has been moved. In other words, if the X-ray non-generation duration time is relatively long, it can be estimated that an anatomical positional shift has occurred between the ROI image and the still image. The measured X-ray non-generation duration time is supplied to a determination unit 13.

The determination unit 13 determines, based on the X-ray non-generation duration time, whether to update the still image. If the determination unit 13 determines to update the still image, a driving control unit 6 enlarges the aperture from the small aperture to the large aperture. If the determination unit 13 determines not to update the still image, the driving control unit 6 maintains the aperture at the small aperture.

Figure 12:
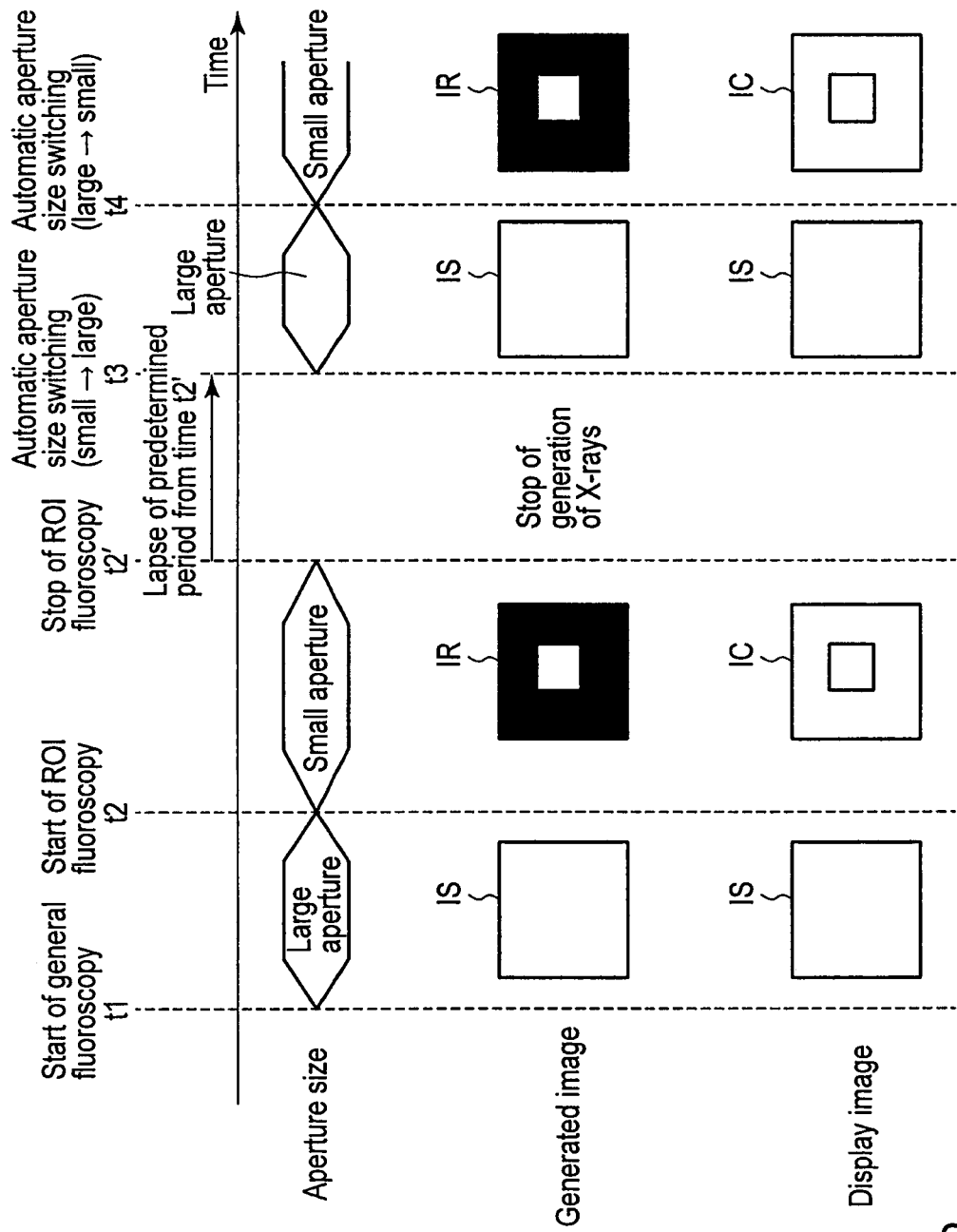
FIG. 12 is a view schematically showing a typical procedure for automatic aperture control processing in ROI fluoroscopy according to Example 3.

An example of automatic aperture control processing in ROI fluoroscopy according to Example 3 will be described below with reference to FIG. 12. FIG. 12 is a view schematically showing a typical procedure for automatic aperture control processing in ROI fluoroscopy according to Example 3. The same processing contents as automatic aperture control processing in ROI fluoroscopy according to Example 1 will be briefly described.

First of all, at time t1, the operator steps on the fluoroscopy switch, and the apparatus performs X-ray fluoroscopy under the control of the driving control unit 6. As described above, in the fluoroscopy mode, the aperture is set to the large aperture, and an image generation unit 81 repeatedly generates a large-aperture image in real time. A display unit 9 displays a large-aperture image IS as a dynamic image in real time.

Upon determining that a large-aperture image suitable for a still image is generated, the operator steps off the fluoroscopy switch and steps on the ROI fluoroscopy switch (time t2). The large-aperture image displayed on the display unit 9 when the operator steps on the ROI fluoroscopy switch is displayed as a still image on the display unit 9. When the operator steps on the ROI fluoroscopy switch, the driving control unit 6 starts ROI fluoroscopy. During the ROI fluoroscopy mode, the image generation unit 81 repeatedly generates an ROI image IR in real time. Every time the ROI image IR is generated, an image combining unit 85 repeatedly generates a composite image IC based on the ROI image IR and the large-aperture image IS stored as a still image in an image storage unit 83 in real time. The display unit 9 displays the generated composite image IC as a dynamic image in real time.

The operator sometimes stops generating X-rays at the time of ROI fluoroscopy. When, for example, the operator steps off all the switches of a foot switch unit 11, an X-ray control unit 7 controls a high voltage generator 25 to stop generating X-rays from an X-ray tube 23. That is, the apparatus stops ROI fluoroscopy. When the apparatus stops the ROI fluoroscopy (time t2'), the X-ray non-generation duration time measurement unit 16 repeatedly measures an X-ray non-generation duration time. The determination unit 13 repeatedly determines whether the measured X-ray non-generation duration time has exceeded a predetermined time set in advance during an X-ray stop period. The operator can arbitrarily set the predetermined time to an arbitrary value via the operation unit 12.

Upon determining that the X-ray non-generation duration time does not exceed the predetermined time, the determination unit 13 determines that there is no need to update the still image. In this case, the driving control unit 6 controls the collimator driving unit 4 to maintain the aperture at the small aperture. An X-ray control unit 7 controls a high voltage generator 25 to make it continuously generate X-rays for fluoroscopy.

Upon determining that the X-ray non-generation duration time has exceeded the predetermined time (time t3), the determination unit 13 determines to update the still image. In this case, the driving control unit 6 controls the collimator driving unit 4 to automatically enlarge the aperture from the small aperture to the large aperture. The X-ray control unit 7 controls the high voltage generator 25 to repeatedly generate X-rays for fluoroscopy from an X-ray tube 23. With this operation, the image generation unit 81 generates the large-aperture image IS.

After the lapse of a predetermined period since the aperture was enlarged to the large aperture (time t4), the driving control unit 6 automatically switches to the ROI fluoroscopy mode. That is, the driving control unit 6 controls the collimator driving unit 4 to automatically reduce the aperture from the large aperture to the small aperture. The X-ray control unit 7 controls the high voltage generator 25 to repeatedly generate X-rays for fluoroscopy. During the ROI fluoroscopy mode, the image generation unit 81 repeatedly generates the ROI image IR in real time. Every time the ROI image IR is generated, the image combining unit 85 repeatedly generates the composite image IC based on the ROI image IR and the large-aperture image IS stored as a new still image in the image storage unit 83 in real time. The display unit 9 displays the generated composite image IC as a dynamic image in real time.

This is the end of the description of an operation example according to Example 3.

As described above, the X-ray diagnostic apparatus according to Example 3 automatically switches the aperture from the small aperture to the large aperture when the X-ray non-generation duration time from when the generation of X-rays is stopped exceeds a predetermined period. This allows the X-ray diagnostic apparatus according to Example 3 to automatically update a still image when an anatomical positional shift occurs between the still image and an ROI image, thereby providing a composite image with a small anatomical positional shift amount. It is therefore not necessary for the operator to change his/her step from one switch to another switch at this time. The operator can therefore update a still image without giving any thought to changing his/her step from one switch to another switch and concentrate on the ablation procedure.

Example 4

A positional shift index according to Example 4 is information associated with the ON state of the ROI fluoroscopy mode and information associated with the OFF state of the mode.

The arrangement of the X-ray diagnostic apparatus according to the fourth embodiment is the same as that shown in FIG. 1.

As described above, a foot switch unit 11 is equipped with an ROI fluoroscopy switch. While the ROI fluoroscopy switch is stepped on, ROI fluoroscopy is set ON. While the ROI fluoroscopy switch is not stepped on, ROI fluoroscopy is set OFF. That is, when the operator steps on the ROI fluoroscopy switch, ROI fluoroscopy is switched ON. When the operator steps on the ROI fluoroscopy switch, the foot switch unit 11 supplies an ON signal to a driving control unit 6 via a system control unit 1. Upon receiving the ON signal, the driving control unit 6 executes ROI fluoroscopy in the above manner. When the operator steps off the ROI fluoroscopy switch, the foot switch unit 11 supplies an OFF signal to the driving control unit 6 via the system control unit 1. Upon receiving the OFF signal, the driving control unit 6 interrupts ROI fluoroscopy, as described above. The ON and OFF signals are supplied to a determination unit 13 via the system control unit 1.

The determination unit 13 determines whether to update a still image in accordance with switching of the ROI fluoroscopy mode. More specifically, the determination unit 13 determines to update a still image, every time the apparatus switches to the ROI fluoroscopy mode. In other cases, the determination unit 13 determines not to update a still image. If the determination unit 13 determines to update a still image, the driving control unit 6 enlarges the aperture from the small aperture to the large aperture. In contrast, if the determination unit 13 determines not to update the still image, the driving control unit 6 maintains the aperture at the small aperture.

Figure 13:
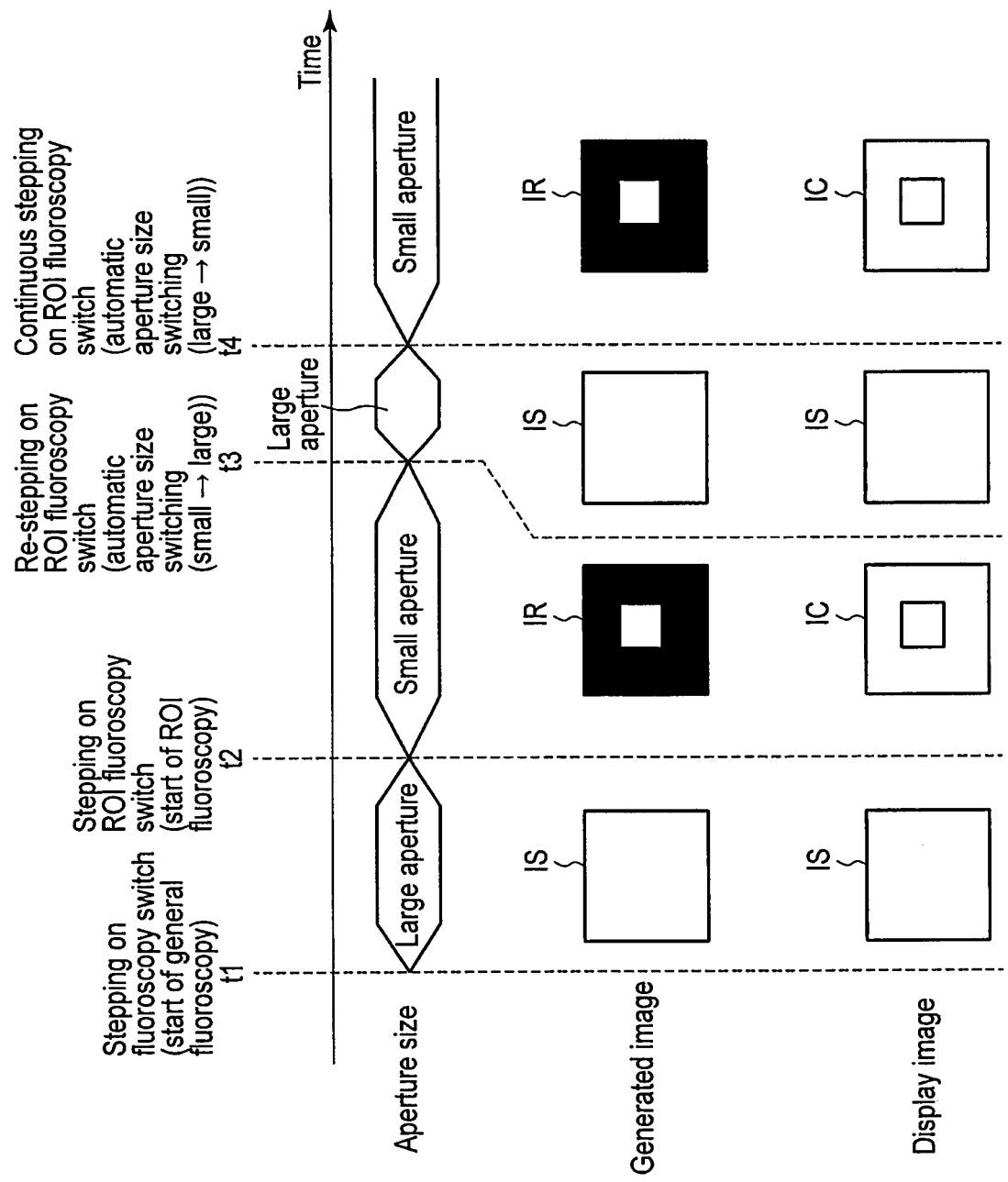
FIG. 13 is a view schematically showing a typical procedure for automatic aperture control processing in ROI fluoroscopy according to Example 4.

An example of automatic aperture control processing in ROI fluoroscopy according to Example 4 will be described below with reference to FIG. 13. FIG. 13 is a view schematically showing a typical procedure for automatic aperture control processing in ROI fluoroscopy according to Example 4. The same processing contents as automatic aperture control processing in ROI fluoroscopy according to Example 1 will be briefly described.

First of all, at time t1, the operator steps on the fluoroscopy switch, and the apparatus performs X-ray fluoroscopy under the control of the driving control unit 6. As described above, in the fluoroscopy mode, the aperture is set to the large aperture, and an image generation unit 81 repeatedly generates a large-aperture image in real time. A display unit 9 displays a large-aperture image IS as a dynamic image in real time. Since the ROI fluoroscopy switch is not stepped on while the fluoroscopy switch is stepped on, the foot switch unit 11 supplies an OFF signal to the determination unit 13. Upon receiving the OFF signal, the determination unit 13 determines not to update the still image.

Upon determining that a large-aperture image suitable for a still image is generated, the operator steps off the fluoroscopy switch and steps on the ROI fluoroscopy switch (time t2). The large-aperture image displayed on the display unit 9 when the operator steps on the ROI fluoroscopy switch is displayed as a still image on the display unit 9. When the operator steps on the ROI fluoroscopy switch, the driving control unit 6 starts ROI fluoroscopy. When the apparatus switches to ROI fluoroscopy, the driving control unit 6 controls a collimator driving unit 4 to automatically reduce the aperture from the large aperture to the small aperture. An X-ray control unit 7 controls a high voltage generator 25 to repeatedly generate X-rays for fluoroscopy from an X-ray tube 23. With this operation, during the ROI fluoroscopy mode, the image generation unit 81 repeatedly generates an ROI image IR in real time. Every time the ROI image IR is generated, an image combining unit 85 repeatedly generates a composite image IC based on the ROI image IR and the large-aperture image IS stored as a still image in an image storage unit 83 in real time. The display unit 9 displays the generated composite image IC as a dynamic image in real time.

As described above, in some cases, a subject P moves or a C-arm 22 or a top 29 moves at the time of ROI fluoroscopy. In such a case, an anatomical positional shift occurs between an ROI image and a still image. In this case, the operator steps on the ROI fluoroscopy switch again (t3). When the operator re-steps on the ROI fluoroscopy switch, the foot switch unit 11 supplies an ON signal to the determination unit 13. Upon receiving the ON signal, the determination unit 13 determines to update the still image. In this case, first of all, the driving control unit 6 controls the collimator driving unit 4 to automatically enlarge the aperture from the small aperture to the large aperture. The X-ray control unit 7 controls the high voltage generator 25 to repeatedly generate X-rays for fluoroscopy from the X-ray tube 23. With this operation, the image generation unit 81 generates the large-aperture image IS.

After the lapse of a predetermined period since the aperture was enlarged to the large aperture (time t4), the driving control unit 6 automatically switches to the ROI fluoroscopy mode. This predetermined period is set to the time during which the large-aperture image IS corresponding to at least one frame can be generated. That is, the driving control unit 6 controls the collimator driving unit 4 to automatically reduce the aperture from the large aperture to the small aperture. The X-ray control unit 7 controls the high voltage generator 25 to repeatedly generate X-rays for fluoroscopy. During the ROI fluoroscopy mode, the image generation unit 81 repeatedly generates the ROI image IR in real time. Every time the ROI image IR is generated, the image combining unit 85 repeatedly generates the composite image IC based on the ROI image IR and the large-aperture image IS stored as a new still image in the image storage unit 83 in real time. The display unit 9 displays the generated composite image IC as a dynamic image in real time.

This is the end of the description of an operation example according to Example 4.

As described above, the X-ray diagnostic apparatus according to Example 4 automatically updates a still image when the operator steps on the ROI fluoroscopy switch. When it is estimated that an anatomical positional shift will occur between a still image and an ROI image, the apparatus can automatically update the still image and can provide a composite image with a little anatomical positional shift amount in the X-ray diagnostic apparatus according to Example 4.

[Effects]

As has been described above, this embodiment can provide an X-ray diagnostic apparatus which can improve procedure efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray tube configured to generate X-rays;
an X-ray detector configured to detect X-rays generated from the X-ray tube and transmitted through a subject;
an aperture-variable collimator mechanism configured to limit a radiation field of X-rays from the X-ray tube;
an image generation unit configured to repeatedly generate a first X-ray image based on an output from the X-ray detector during a period in which an aperture of the collimator mechanism is a first aperture and to repeatedly generate a second X-ray image based on an output from the X-ray detector during a period in which the aperture is a second aperture smaller than the first aperture;
a combining unit configured to repeatedly generate a composite image based on a latest second X-ray image of the repeatedly generated second X-ray images and a specific first X-ray image of the repeatedly generated first X-ray images for the second X-ray image is generated;
a display unit configured to display the repeatedly generated composite image as a dynamic image in real time;
a determination unit configured to determine whether to update the first X-ray image in the composite image, based on an index associated with an anatomical positional shift between the first X-ray image and the second X-ray image; and
a control unit configured to enlarge the aperture of the collimator mechanism from the second aperture to the first aperture by controlling the collimator mechanism when the determination unit determines to update the first X-ray image and to maintain the aperture of the collimator mechanism at the second aperture by controlling the collimator mechanism when the determination unit determines not to update the first X-ray image.

2. The X-ray diagnostic apparatus of claim 1, further comprising:
a top on which the subject is placed; and
a top support mechanism configured to support to move the top,
wherein the index is a spatial position of the top, and
the determination unit determines whether to update the first X-ray image, based on a threshold and a difference between a first spatial position at the time of generation of the first X-ray image and a second spatial position at the time of generation of the second X-ray image.

3. The X-ray diagnostic apparatus of claim 1, wherein the index is a generation duration time of X-rays from the X-ray tube in real time, and
the determination unit determines whether to update the first X-ray image, based on the generation duration time and a threshold.

4. The X-ray diagnostic apparatus of claim 1, wherein the index is a non-generation duration time of X-rays from the X-ray tube in real time, and
the determination unit determines whether to update the first X-ray image, based on the non-generation duration time and a threshold.

5. The X-ray diagnostic apparatus of claim 1, further comprising an input unit configured to switch between an ON state and OFF state of an ROI fluoroscopy mode,
wherein the index is information associated with the ON state of the ROI fluoroscopy mode and information associated with the OFF state, and
the determination unit determines to update the first X-ray image for the ROI fluoroscopy mode is switched to the ON state via the input unit.

6. The X-ray diagnostic apparatus of claim 1, further comprising an arm on which the X-ray tube and the X-ray detector are pivotally mounted,
the index is a spatial position of the arm, and
the determination unit determines whether to update the first X-ray image, based on a threshold and a difference between a first spatial position at the time of generation of the first X-ray image and a second spatial position at the time of generation of the second X-ray image.

7. The X-ray diagnostic apparatus of claim 1, wherein the specific first X-ray image is the latest X-ray image of the repeatedly generated first X-ray images.

* * * * *